United States Patent
Chen et al.

(10) Patent No.: US 7,005,519 B1
(45) Date of Patent: Feb. 28, 2006

(54) TETRAAZAPORPHYRIN COMPOUNDS

(75) Inventors: Chin-Ti Chen, Taipei (TW); Hsiu-Chih Yeh, Taipei (TW)

(73) Assignee: Academia Sinica, Taipei (TW)

( * ) Notice: Subject to any disclaimer, the term of this patent is extended or adjusted under 35 U.S.C. 154(b) by 0 days.

(21) Appl. No.: 10/922,138

(22) Filed: Aug. 18, 2004

(51) Int. Cl.
| | |
|---|---|
| *C07B 47/00* | (2006.01) |
| *A61B 5/055* | (2006.01) |
| *A61B 10/00* | (2006.01) |
| *C07F 5/10* | (2006.01) |
| *A61K 31/555* | (2006.01) |

(52) U.S. Cl. .................. 540/145; 424/9.362; 424/9.61; 534/15; 514/185; 514/410

(58) Field of Classification Search ............. 424/9.362, 424/9.61; 540/145; 534/15; 514/185, 410
See application file for complete search history.

(56) References Cited

U.S. PATENT DOCUMENTS

| | | | | |
|---|---|---|---|---|
| 4,814,256 A | * | 3/1989 | Aldag et al. ........... | 430/270.16 |
| 5,998,093 A | * | 12/1999 | Tomura et al. ........ | 430/270.16 |

OTHER PUBLICATIONS

Sheldon, Roger A., Metalloporphyrins in Catalytic Oxidations., 1994., Marcel Dekker, Inc. p. 218.*
Vagin et al., Synthesis and Characterization of (Octaaryltetraazaporphyrinato)Indium(III) Complexes for Optical Limiting., Inorg. Chem. 42(8) 2003. pp. 2683-2694.*
Vagin et al., Synthesis and Spectroscopic Properties of Non-Symmetrical Benzo-Annulated Porphyrazines and their Metal Complexes. Eur. J. Org. Chem. 2002, pp. 2859-2865.*
Kobayashi, "Meso-Azaporphyrins and Their Analogues", The Porphyrin Handbook 13:301-360, 2000.
Vagin et al., "synthesis and Characterization of (Octaaryltetraazaporphyrinato)indium(III) Complexes for Optical Limiting", Inorganic Chemistry 42:2683-2694, 2003.

* cited by examiner

*Primary Examiner*—James O. Wilson
*Assistant Examiner*—Matthew L. Fedowitz

(74) *Attorney, Agent, or Firm*—Fish & Richardson P.C.

(57) ABSTRACT

This invention relates to a method of preparing a compound of formula (I):

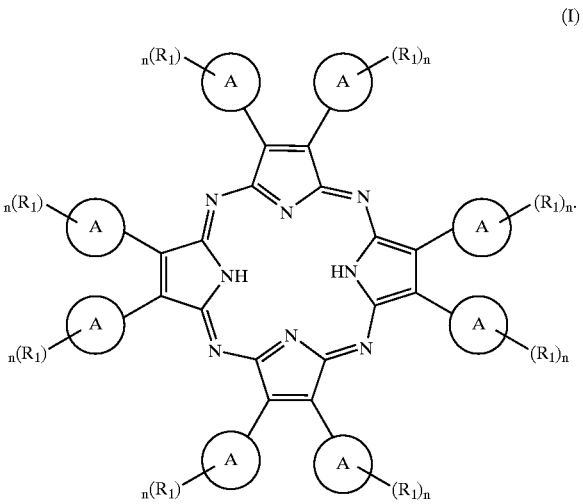

The method includes reacting one or more compounds of formula (II):

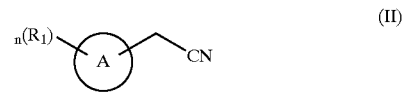

in the presence of a base and a halogenating agent. In formulas (I) and (II) above, each A, independently, is aryl or heteroaryl; each n, independently, is 0–3; and each $R_1$, independently, is $C_1$–$C_{10}$ alkyl, $C_3$–$C_{20}$ cycloalkyl, $C_3$–$C_{20}$ heterocycloalkyl, aryl, heteroaryl, halo, cyano, nitro, $OR_a$, $NR_aR_b$, $SiR_aR_bR_c$, $COOR_a$, $OC(O)R_a$, $C(O)NR_aR_b$, $N(R_a)$—$C(O)R_b$, or $SO_3R_a$; wherein each of $R_a$, $R_b$, and $R_c$, independently, is H, $C_1$–$C_{10}$ alkyl, $C_3$–$C_{20}$ cycloalkyl, $C_3$–$C_{20}$ heterocycloalkyl, aryl, or heteroaryl; thereby producing the compound of formula (I) in a one-pot reaction. This invention also relates to the compounds prepared by the method described above.

25 Claims, No Drawings

TETRAAZAPORPHYRIN COMPOUNDS

BACKGROUND

Tetraazaporphyrin compounds, featured by a conjugated $C_8N_8$ ring fused with four pyrrole groups, have a planar and highly symmetrical structure. Given this unique structure, extensive studies have been conducted on their non-linear optical properties and their uses as electrooptical materials.

Conventional methods for preparing tetraazaporphyrin compounds are tedious and result in low yields. Further, as tetraazaporphyrin compounds generally have low solubility in organic solvents, they cannot be easily processed for electronic applications. Further, Thus, there exists a need to develop a simple method for preparing tetraazaporphyrin compounds with improved solubility.

SUMMARY

This invention is based on an unexpected discovery that certain tetraazaporphyrin compounds can be prepared by a one-pot reaction and have improved solubility in organic solvents.

In one aspect, this invention features a method of preparing a tetraazaporphyrin compound of formula (I):

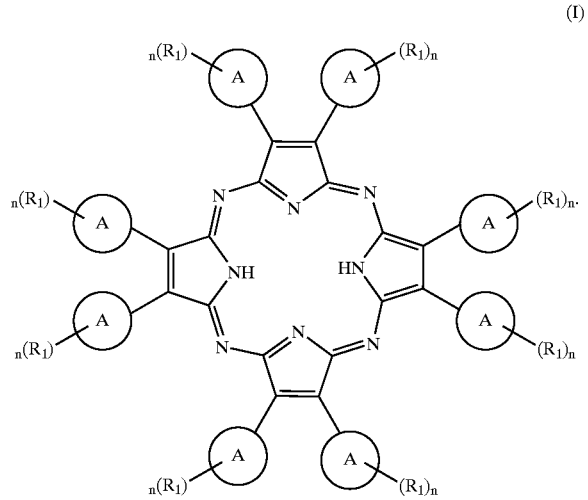

The method includes reacting one or more compounds of formula (II):

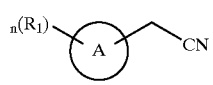

in the presence of a base and a halogenating agent, thereby producing the compound of formula (I) in a one-pot reaction. In formulas (I) and (II), each A, independently, is aryl or heteroaryl; each n, independently, is 0–3; and each $R_1$, independently, is $C_1$–$C_{10}$ alkyl, $C_3$–$C_{20}$ cycloalkyl, $C_3$–$C_{20}$ heterocycloalkyl, aryl, heteroaryl, halo, cyano, nitro, $OR_a$, $NR_aR_b$, $SiR_aR_bR_c$, $COOR_a$, $OC(O)R_a$, $C(O)NR_aR_b$, $N(R_a)$—$C(O)R_b$, or $SO_3R_a$; wherein each of $R_a$, $R_b$, and $R_c$, independently, is H, $C_1$–$C_{10}$ alkyl, $C_3$–$C_{20}$ cycloalkyl, $C_3$–$C_{20}$ heterocycloalkyl, aryl, or heteroaryl. For example, in a compound of formula (I), A can be phenyl; n can be 1; and $R_1$ can be at o-, m-, or p-position and can be $CH_3$, $CF_3$, Cl, $OCH_3$, or $OC_{12}H_{25}$. Preferrably, only one compound of formula (II) is used to prepare a tetraazaporphyrin compound of formula (I).

A tetraazaporphyrin compound of formula (I) can further react with a salt containing a metal ion, thereby producing a metal complex. Examples of such a salt includes a zinc salt, a nickel salt, a palladium salt, an aluminum salt, or a magnesium salt.

The term "alkyl" mentioned herein refers to a saturated or unsaturated, linear or branched, non-aromatic hydrocarbon moiety, such as —$CH_3$, —$CH_2$—$CH$=$CH_2$, or branched —$C_3H_7$. The term "cycloalkyl" refers to a saturated or unsaturated, non-aromatic, cyclic hydrocarbon moiety, such as cyclohexyl or cyclohexen-3-yl. The term "heterocycloalkyl" refers to a saturated or unsaturated, non-aromatic, cyclic moiety having at least one ring heteroatom (e.g., N, O, or S), such as 4-tetrahydropyranyl or 4-pyranyl. The term "aryl" refers to a hydrocarbon moiety having one or more aromatic rings. Examples of an aryl moiety include phenyl, phenylene, naphthyl, naphthylene, pyrenyl, anthryl, phenanthryl, and ferrocenyl. The term "heteroaryl" refers to a moiety having one or more aromatic rings that contain at least one heteroatom (e.g., N, O, or S). Examples of a heteroaryl moiety include furyl, furylene, fluorenyl, pyrrolyl, thienyl, oxazolyl, imidazolyl, thiazolyl, pyridyl, pyrimidinyl, quinazolinyl, quinolyl, isoquinolyl and indolyl.

Alkyl, cycloalkyl, heterocycloalkyl, aryl, and heteroaryl mentioned herein include both substituted and unsubstituted moieties, unless specified otherwise. Possible substituents on cycloalkyl, heterocycloalkyl, aryl, and heteroaryl include $C_1$–$C_{10}$ alkyl, $C_2$–$C_{10}$ alkenyl, $C_2$–$C_{10}$ alkynyl, $C_3$–$C_8$ cycloalkyl, $C_5$–$C_8$ cycloalkenyl, $C_1$–$C_{10}$ alkoxy, aryl, aryloxy, heteroaryl, heteroaryloxy, amino, $C_1$–$C_{10}$ alkylamino, $C_1$–$C_{20}$ dialkylamino, arylamino, diarylamino, hydroxyl, halogen, thio, $C_1$–$C_{10}$ alkylthio, arylthio, $C_1$–$C_{10}$ alkylsulfonyl, arylsulfonyl, acylamino, aminoacyl, amidino, guanidine, ureido, cyano, nitro, acyl, acyloxy, carboxyl, and carboxylic ester. On the other hand, possible substituents on alkyl include all of the above-recited substituents except $C_1$–$C_{10}$ alkyl, $C_2$–$C_{10}$ alkenyl, and $C_2$–$C_{10}$ alkynyl. Cycloalkyl, heterocycloalkyl, aryl, and heteroaryl can also be fused with each other.

The term "halogenating agent" refers to any suitable reagent that can incorporate halogen atoms into organic compounds. Examples of halogenating agents include halogen (e.g., $Cl_2$, $Br_2$, or $I_2$), sulfuryl halide (e.g., $SO_2Cl_2$, $SO_2Br_2$, or $SO_2I_2$), thionyl halide (e.g., $SOCl_2$, $SOBr_2$, or $SOI_2$), chlorate salts (e.g., $NaClO_3$, $PClO_3$, or $Ca(ClO_3)_2$), hypochlorite salts (e.g., NaClO, PClO, or $Ca(ClO)_2$), hypobromite salts (e.g., NaBrO), hypoiodite salts (e.g., NaIO), N-chlorosuccinimide, N-bromosuccinimide, and N-iodosuccinimide. Examples of bases that can be used in the method of this invention include alkoxide salts, such as lithium, sodium, potassium, or magnesium salt of methoxide, ethoxide, propoxide, or t-butoxide, as well as other suitable bases known in the art. The method of this invention affords a tetraazaporphyrin compound in a one-pot reaction, i.e., without isolating any intermediates from the reaction.

In another aspect, this invention features a tetraazaporphyrin compound of formula (I), in which each A is phenyl; each n, independently, is 1–5; and each $R_1$, independently, is $C_1$–$C_{10}$ alkyl, $C_3$–$C_{20}$ cycloalkyl, $C_3$–$C_{20}$ heterocycloalkyl, aryl, heteroaryl, halo, cyano, nitro, $OR_a$, $NR_aR_b$, $SiR_aR_bR_c$, $COOR_a$, $OC(O)R_a$, $C(O)NR_aR_b$, $N(R_a)$—$C(O)R_b$, or —$SO_3R_a$; provided that if n is 1 and $R_1$ is at m-position, $R_1$ is unsubstituted $C_1$–$C_{10}$ alkyl, $C_3$–$C_{20}$ cycloalkyl, $C_3$–$C_{20}$ heterocycloalkyl, aryl, heteroaryl, halo, cyano, nitro, $OR_a$, $NR_aR_b$, $SiR_aR_bR_c$, $COOR_a$, $OC(O)R_a$, $C(O)NR_aR_b$, $N(R_a)$ —$C(O)R_b$, or $SO_3R_a$; and if n is 1 and $R_1$ is at p-position, $R_1$ is $C_5$–$C_{10}$ alkyl, $C_3$–$C_{20}$ cycloalkyl, $C_3$–$C_{20}$ heterocycloalkyl, aryl, heteroaryl, halo, cyano, nitro, $OR_a$, $NR_aR_b$, $SiR_aR_bR_c$, $COOR_a$, $OC(O)R_a$, $C(O)NR_aR_b$, $N(R_a)$—$C(O)R_b$, or $SO_3R_a$; wherein each of $R_a$, $R_b$, and $R_c$, independently, is H, $C_1$–$C_{10}$ alkyl, $C_3$–$C_{20}$ cycloalkyl, $C_3$–$C_{20}$ heterocycloalkyl, aryl, or heteroaryl; or a metal complex thereof. Referring to formula (I), a subset of compounds described above are those in which n is 1; and $R_1$ can be at o-, m-, or p-position and can be $CH_3$, $CF_3$, Cl, $OCH_3$, or $OC_{12}H_{25}$.

In still another aspects, this invention features a tetraazaporphyrin compound of formula (I), in which each A, independently, is heteroaryl or fused aryl; each n, independently, is 0–3; and each $R_1$, independently, is $C_1$–$C_{10}$ alkyl, $C_3$–$C_{20}$ cycloalkyl, $C_3$–$C_{20}$ heterocycloalkyl, aryl, heteroaryl, halo, cyano, nitro, $OR_a$, $NR_aR_b$, $SiR_aR_bR_c$, $COOR_a$, $OC(O)R_a$, $C(O)NR_aR_b$, $N(R_a)$—$C(O)R_b$, or $SO_3R_a$; wherein each of $R_a$, $R_b$, and $R_c$, independently, is H, $C_1$–$C_{10}$ alkyl, $C_3$–$C_{20}$ cycloalkyl, $C_3$–$C_{20}$ heterocycloalkyl, aryl, or heteroaryl; or a metal complex thereof.

The tetraazaporphyrin compounds described above include the compounds themselves, as well as their salts and metal complexes, if applicable. A salt, for example, can be formed between an anion and a positively charged group (e.g., amino) on a tetraazaporphyrin compound. Suitable anions include chloride, bromide, iodide, sulfate, bisulfate, sulfamate, nitrate, phosphate, citrate, methanesulfonate, trifluoroacetate, maleate, succinate, fumarate, tartrate, salicylate, lactate, naphthalenesulfonate, and acetate. Likewise, a salt can also be formed between a cation and a negatively charged group (e.g., carboxylate) on a tetraazaporphyrin compound. Suitable cations include sodium ion, potassium ion, magnesium ion, calcium ion, and an ammonium cation such as tetramethylammonium ion. The tetraazaporphyrin compounds also include those salts containing quaternary nitrogen atoms. A metal complex can be formed between any of the tetraazaporphyrin compounds described above and a salt containing a metal ion. Examples of metal ions include zinc ion, nickel ion, palladium ion, aluminum ion, or magnesium ion.

Shown below are exemplary compounds of this invention.

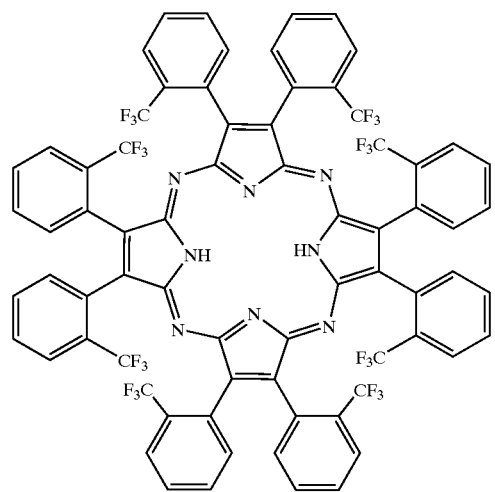

Compound 1

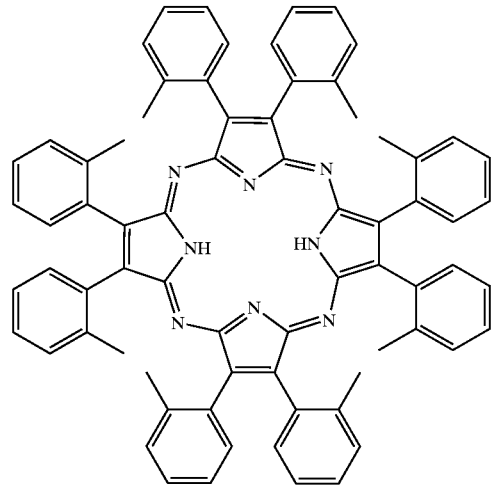

Compound 2

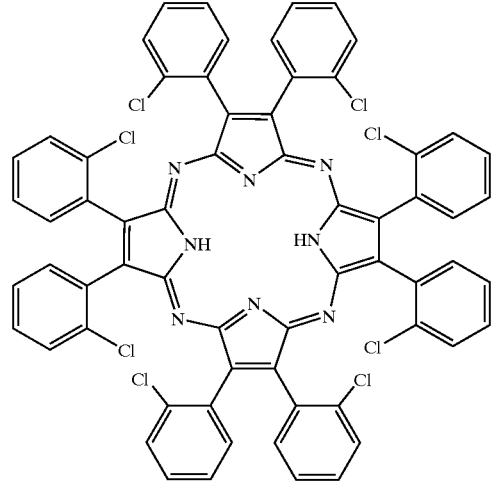

Compound 3

Compound 4
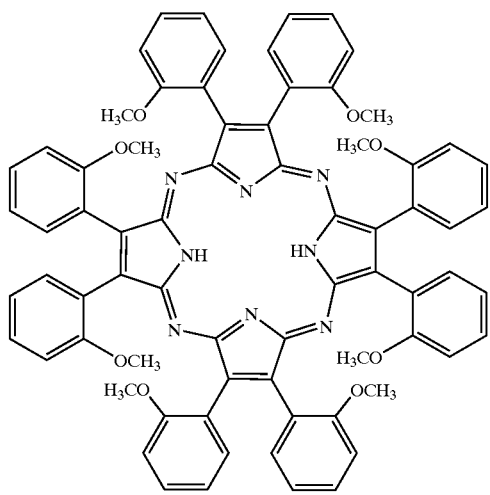
Compound 5
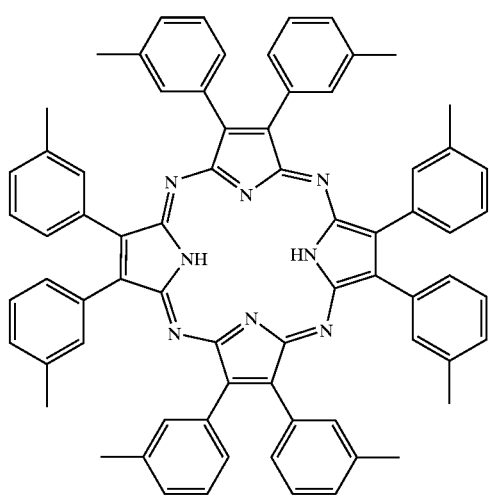
Compound 6
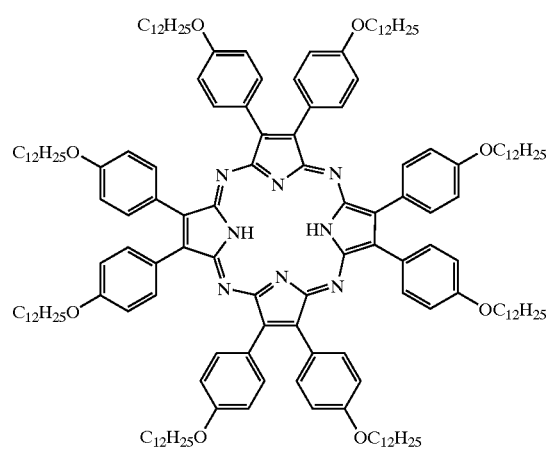
Compound 7
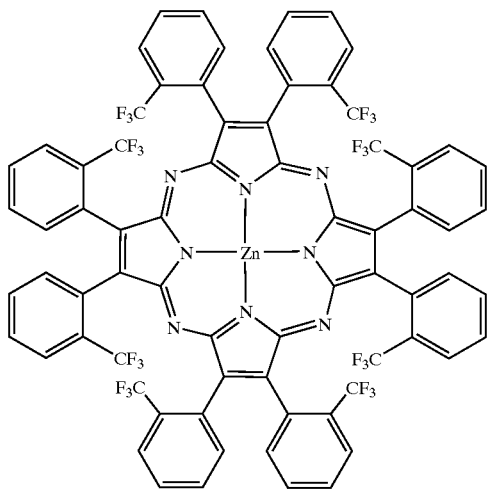
Compound 8
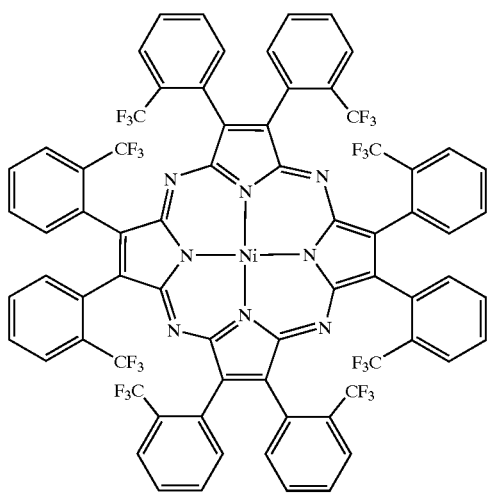
Compound 9
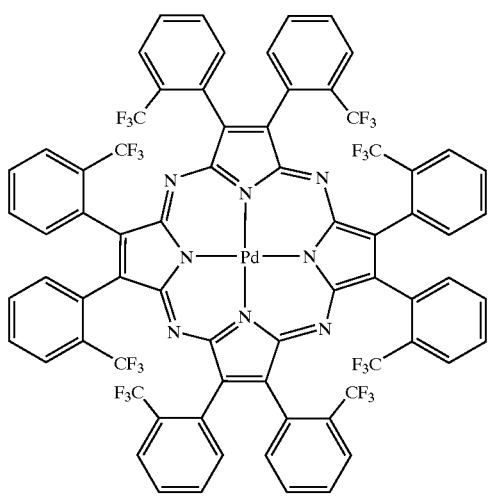

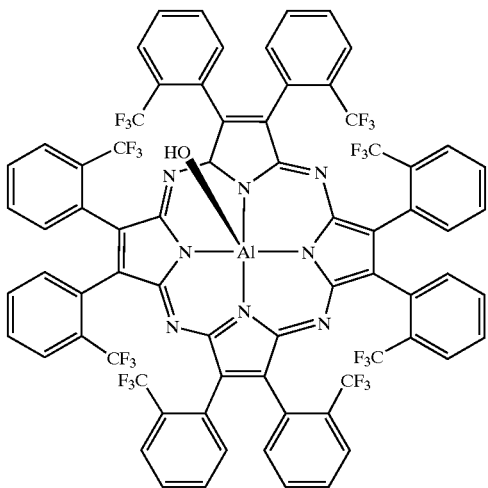

Compound 10

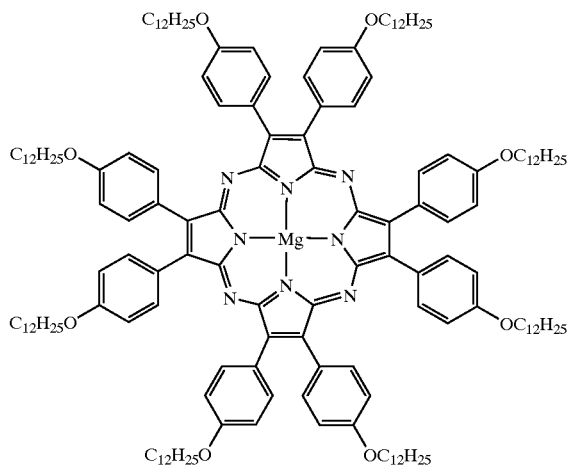

Compound 11

The details of one or more embodiments of the invention are set forth in the description below. Other features, objects, and advantages of the invention will be apparent from the description and from the claims.

DETAILED DESCRIPTION

This invention relates to a facile method of preparing tetraazaporphyrin compounds. Specifically, in the presence of a strong base (e.g., sodium methoxide) and a halogenating agent (e.g., iodine), arylacetonitrile or heteroarylacetonitrile molecules readily react with themselves to form octaaryltetraazaporphyrin or octaheteroaryltetraazaporphyrin in a one-pot reaction. Since it is not necessary to isolate any intermediates from the reaction, the yields of the products are greatly improved.

The method of this invention can be used to prepare octaphenyltetraazaporphyrin compounds containing ortho substituents on the phenyl rings. It is known that a diphenyl-substituted dinitrile is difficult to synthesize if it contains substituents at the ortho positions on the phenyl rings due to the steric hindrance of the substituents. To date, there has been no literature reporting the synthesis of octaphenyltetraazaporphyrin compounds containing ortho substituents on the phenyl rings, as they generally have to be synthesized from the just-mentioned diphenyl-substituted dinitrile. Since such diphenyl-substituted dinitrile does not necessarily form in the method of this invention, this method can be used readily to prepare octaphenyltetraazaporphyrin compounds containing ortho substituents on the phenyl rings.

The tetraazaporphyrin compound obtained from the above-described method can further react with a salt containing a metal ion, thereby producing a metal complex. The metal ion can be monovalent, divalent, trivalent, or tetravalent. The reaction conditions used for incorporating metal ions into tetraazaporphyrins are well known in the art and include, for example, those described in Adler et al., (1970) *J. Inorg. Nucl. Chem.*, 32, 2443–2445; and Buehler, J. W., in *The Porphyrins*; Dolphin, D. Ed.; Academic Press: New York, 1978; pp. 389–483.

Schemes 1 and 2 below depict the syntheses of exemplary compounds 1–6 and compounds 7–11 (i.e., metal complexes of compound 1), respectively. Details of preparation of these compounds are provided in Examples 1–11, respectively.

Scheme 1

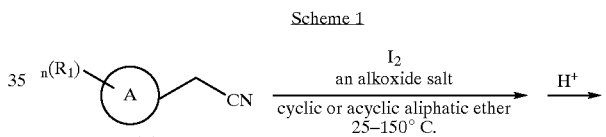

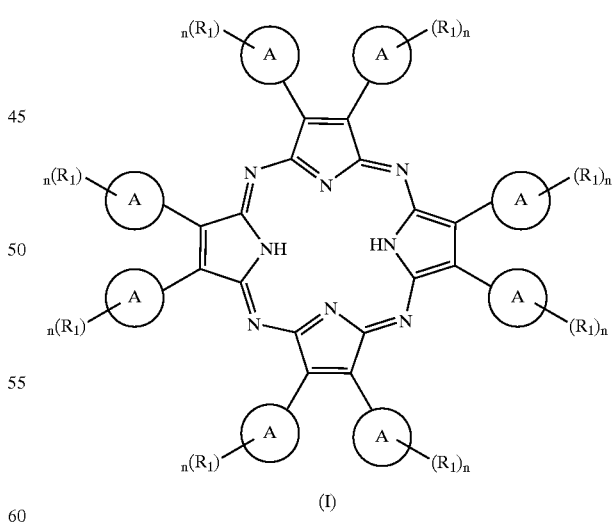

Compounds 1–6:
A = phenyl
n = 1
$R_1$ = $CH_3$, $CF_3$, Cl, $OCH_3$, or $OCH_{12}H_{25}$ Scheme 2

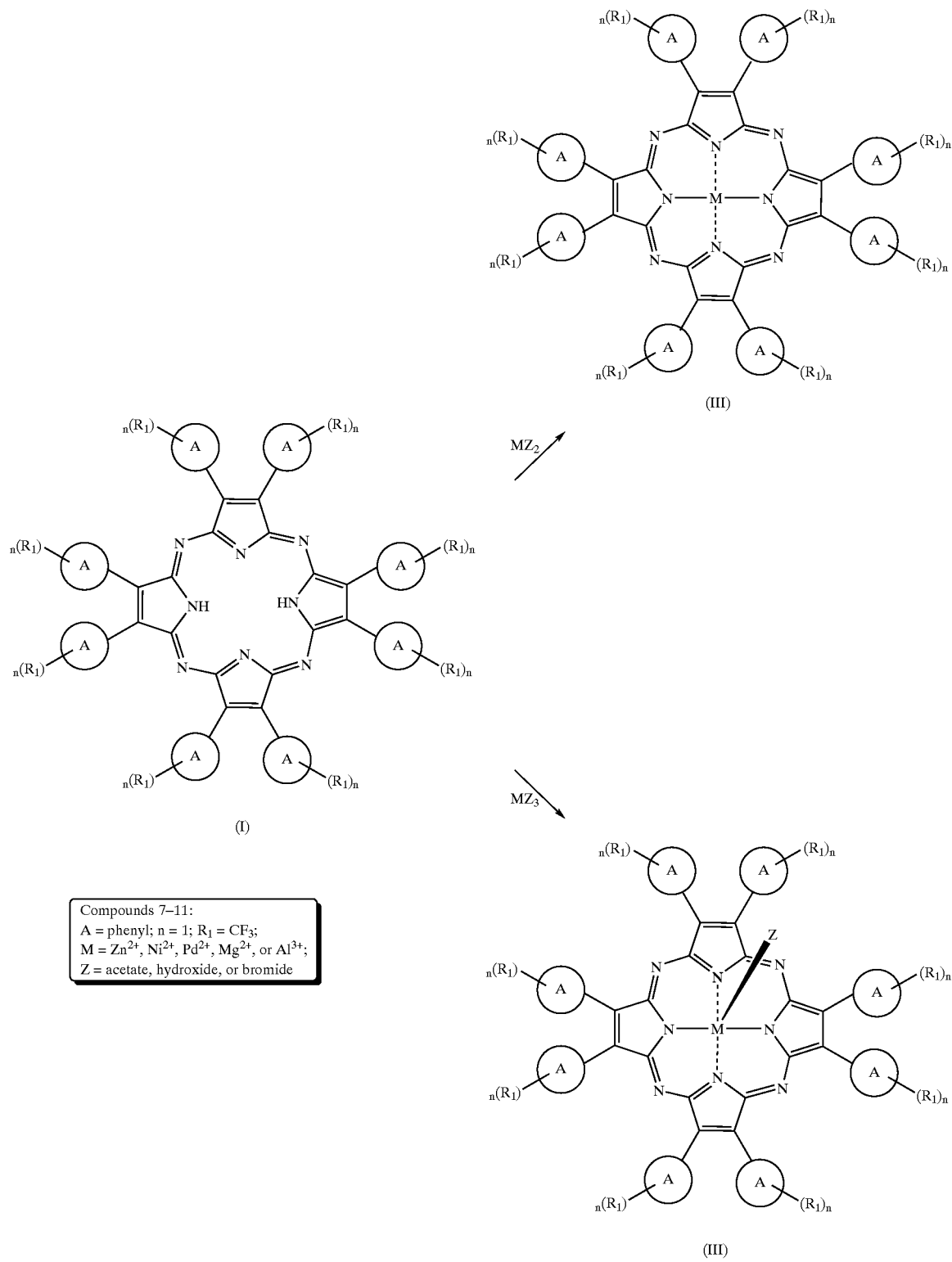

Compounds 7–11:
A = phenyl; n = 1; $R_1 = CF_3$;
M = $Zn^{2+}$, $Ni^{2+}$, $Pd^{2+}$, $Mg^{2+}$, or $Al^{3+}$;
Z = acetate, hydroxide, or bromide Referring to Scheme 1, to obtain 1 equivalent of compound (I), 8 equivalents of compound (II) are first treated with an alkoxide salt and iodine. The reaction mixture can then be kept under reflux for, e.g., 24 hours. After the reaction is complete, an acid solution is added to the mixture to form compound (I), which is subsequently collected (e.g., via filtration) and purified (e.g., by washing with a mixture of water and methanol). Compound (I) thus obtained can further react with a salt containing a metal ion to afford a metal complex. See Scheme 2.

Solvents used in the method of this invention can be cyclic or acyclic ethers, such as tetrahydrofuran, 2-methyltetrahydrofuran, tetrahydropyran, 1,4-dioxane, dibutyl ether, diphenyl ether, or ethylene glycol dimethyl ether. Other suitable solvents can also be used in this method.

The reaction temperature used in the above-described method can be the same as or lower than the boiling point of the solvent, and is preferably below 150° C.

A tetraazaporphyrin compound thus obtained can be further purified by a known method such as column chromatography, high pressure liquid chromatography, recrystallization, or sublimation.

Also within the scope of the invention are tetraazaporphyrin compounds or their metal complexes described in the Summary section above. These compounds have strong absorption at the wavelength of 310–380 and 580–680 nm. The metal complexes can generate fluorescence after absorbing light at a certain wavelength. These compounds exhibit improved solubility in organic solvents and can be readily processed in electronic applications. For example, soluble tetraazaporphyrin compounds can be used as high density optical recording media, such as CD-R, DVD-R, and HD-DVD-R. Indeed, the lasers used in manufacturing CD-R, DVD-R, and HD-DVD-R have a wavelength of 780 nm, 635 nm, and 405 nm, respectively, and are strongly absorbed by the tetraazaporphyrin compounds of this invention. Soluble tetraazaporphyrin compounds can also be used in applications such as electrooptical sensors, electrochromics, electroluminescent display, and graphic reproduction.

The specific examples below are to be construed as merely illustrative, and not limitative of the remainder of the disclosure in any way whatsoever. Without further elaboration, it is believed that one skilled in the art can, based on the description herein, utilize the present invention to its fullest extent. All publications cited herein are hereby incorporated by reference in their entirety.

EXAMPLE 1

Synthesis of octa(ortho-trifluormethylphenyl)tetraazaporphyrin (Compound 1)

Sodium methoxide (13.5 g, 0.25 mol) was added in dried THF (200 mL) and the mixture thus obtained was kept at 0° C. in a cooling bath. To this mixture were added ortho-trifluoromethylbenzyl cyanide (9.5 g, 0.05 mol) and iodine (12.7 g, 0.05 mol). The cooling bath of the reaction was replaced with an oil bath. After refluxing for 24 hours, the reaction mixture was cooled down to room temperature. Then, a 3 M aqueous HCl solution (40 mL) was added to the mixture. Some of THF (~140 mL) was subsequently removed under reduced pressure. A 1:1 mixture (by volume) of water and methanol (150 mL) was then added to the remaining mixture. After stirring for 10 minutes, the resultant mixture was allowed to sit for at least 6 hours. Compound 1 (a dark solid) was isolated by filtration, washed with a 1:1 mixture (by volume) of water and methanol, and vacuum-dried. The yield was 40% (3.8 g). UV-Vis: $\lambda_{max}$ (THF)=350, 530(sh), 566, 610(sh), 635 nm.

EXAMPLE 2

Synthesis of octa(ortho-methylphenyl)tetraazaporphyrin (Compound 2)

Compound 2 was prepared in a manner similar to that described in Example 1 except that ortho-methylbenzyl cyanide (6.37 mL, 50 mmol) was used as a starting material. The crude product was purified by washing with a mixture of methanol and water (8:2). The yield was 24% (1.56 g). UV-Vis: $\lambda_{max}$ (THF)=358, 425(sh), 550(sh), 585, 652 nm.

EXAMPLE 3

Synthesis of octa(ortho-chlorophenyl)tetraazaporphyrin (Compound 3)

Compound 3 was prepared in a manner similar to that described in Example 1 except that ortho-chlorobenzyl cyanide (7.817 mL, 50 mmol) was used as a staring material. The crude product was purified by washing with a mixture of methanol and water (8:2). The yield was 43% (3.23 g). UV-Vis: $\lambda_{max}$ (THF)=359, 550(sh), 583, 651 nm.

EXAMPLE 4

Synthesis of octa(ortho-methoxyphenyl)tetraazaporphyrin (Compound 4)

Compound 4 was prepared in a manner similar to that described in Example 1 except that ortho-methoxybenzyl cyanide (7.5 g, 50 mmol) was used a starting material. The crude product was purified by washing with a mixture of methanol and water (8:2). The yield was 23% (1.7 g). UV-Vis: $\lambda_{max}$ (THF)=351, 450(sh), 565(sh), 600, 667 nm.

EXAMPLE 5

Synthesis of octa(meta-methylphenyl)tetraazaporphyrin (Compound 5)

Compound 5 was prepared in a manner similar to that described in Example 1 except that meta-methylbenzyl cyanide (6.7 mL, 50 mmol) was used a starting material. The crude product was purified by washing alternatively with methanol and water. The yield was 35% (2.3 g). UV-Vis: $\lambda_{max}$ (THF)=351, 435(sh), 565(sh), 601, 667 nm.

EXAMPLE 6

Synthesis of octa(para-dodecyloxyphenyl)tetraazaporphyrin (Compound 6)

Compound 6 was prepared in a manner similar to that described in Example 1 except that para-dodecyloxybenzyl cyanide (3.1 g, 10 mmol) was used as a starting material. The crude product was first purified by washing alternatively with methanol and water, and then purified by column chromatography (silica gel, 10% dichloromethane in hexane). The yield was 10% (0.30 g). UV-Vis: $\lambda_{max}$ (THF)=342, 377, 504, 619, 685 nm.

EXAMPLE 7

Synthesis of the Zinc Complex of octa(ortho-trifluormethylphenyl)tetraazaporphyrin (Compound 7)

Compound 1 (2.93 g, 2 mmol) was first dissolved in DMF (20 mL). Zinc acetate (3.67 g, 20 mmol) was added to the solution obtained above. The mixture was then kept under reflux for 24 hours. DMF was subsequently removed under reduced pressure and the residue solid was mixed with THF. The mixture was filtered and dried to give a crude product. The crude product was purified by train-sublimation (three zone temperatures: 350, 230, and 120° C.) to give compound 7. The yield was 70% (2.1 g). UV-Vis: $\lambda_{max}$ (THF)=354, 555, 604 nm. Fluorescence: $\lambda_{max}$ (THF)=626 nm.

EXAMPLE 8

Synthesis of the Nickel Complex of octa(ortho-trifluormethylphenyl)tetraazaporphyrin (Compound 8)

Compound 8 was prepared in a manner similar to that described in Example 7 except that nickel acetate tetrahydrate (2.54 g, 10 mmol) and compound 1 (1.45 g, 1 mmol) were used as starting materials. The yield was 75% (1.16 g). UV-Vis: $\lambda_{max}$ (THF)=326, 346, 549 (sh), 596 nm.

EXAMPLE 9

Synthesis of the Palladium Complex of octa(ortho-trifluormethylphenyl)-tetraazaporphyrin (Compound 9)

Compound 9 was prepared in a manner similar to that described in Example 7 except that palladium acetate tetrahydrate (0.84 g, 3.3 mol) and compound 1 (2.38 g, 1.64 mmol) were used as starting materials. The yield was 75% (1.9 g). UV-Vis: $\lambda_{max}$ (THF)=315, 344, 538, 586 nm.

EXAMPLE 10

Synthesis of the Aluminum Hydroxy Complex of octa(ortho-trifluormethylphenyl)tetraazaporphyrin (Compound 10)

Compound 1 (1.45 g, 1 mmol) and aluminum chloride (1.3 g, 10 mmol) were first mixed in quinoline (10 mL). After the mixture was heated to about 200° C. and kept at that temperature for 6 hours, the mixture was cooled down to room temperature and excess amount of methanol (~10 mL) was added. Both quinoline and methanol were then removed under reduced pressure. The solid residue was mixed with THF. The mixture was then filtered and the filtrate was dried to give a crude product. The crude product was purified by train-sublimation (three zone temperatures: 360, 220, and 120° C.) to give compound 10. The yield was 20% (0.3 g). UV-Vis: $\lambda_{max}$ (THF)=356, 552, 602, 634 nm. Fluorescence: $\lambda_{max}$ (THF)=612 nm.

EXAMPLE 11

Synthesis of the Magnesium Complex of octa-(para-dodecyloxyphenyl)-tetraazaporphyrin (Compound 11)

Compound 6 (0.24 g, 0.1 mmol) was first dissolved in DMF (5 mL). Magnesium bromide hexahydrate (0.29 g, 1.0 mmol) was then added to the solution obtained above. The mixture was kept under reflux for 24 hours. DMF was subsequently removed under reduced pressure. The solid residue was mixed with THF. The mixture was filtered and the filtrate was dried to give a crude product. The crude product was purified by column chromatography (10% dichloromethane in hexane) to give compound 11. The yield was 85% (0.21 g). UV-Vis: $\lambda_{max}$ (THF)=385, 494, 600, 655 nm. Fluorescence: $\lambda_{max}$ (THF) 667 nm.

Other Embodiments

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the present invention, and without departing from the spirit and scope thereof, can make various changes and modifications of the invention to adapt it to various usages and conditions. Thus, other embodiments are also within the scope of the following claims.

What is claimed is:

1. A method of preparing a compound of formula (I):

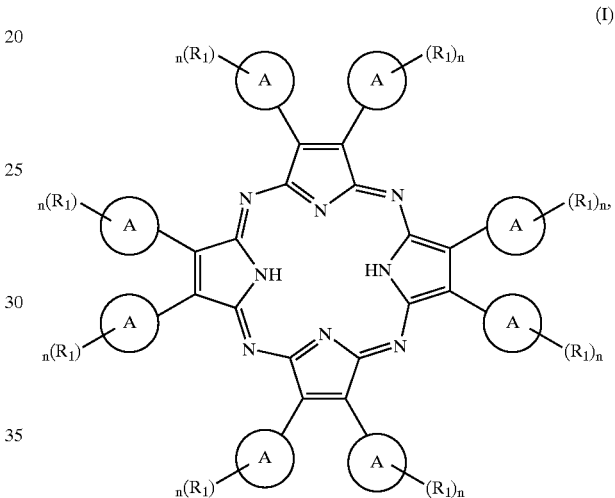

the method comprising
reacting one or more compounds of formula (II):

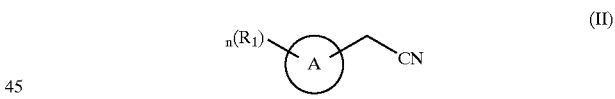

in the presence of a base and a halogenating agent; wherein
each A, independently, is aryl or heteroaryl;
each n, independently, is 0–3; and
each $R_1$, independently, is $C_1$–$C_{10}$ alkyl, $C_3$–$C_{20}$ cycloalkyl, $C_3$–$C_{20}$ heterocycloalkyl, aryl, heteroaryl, halo, cyano, nitro, $OR_a$, $NR_aR_b$, $SiR_aR_bR_c$, $COOR_a$, $OC(O)R_a$, $C(O)NR_aR_b$, $N(R_a)$—$C(O)R_b$, or $SO_3R_a$; wherein each of $R_a$, $R_b$, and $R_c$, independently, is H, $C_1$–$C_{10}$ alkyl, $C_3$–$C_{20}$ cycloalkyl, $C_3$–$C_{20}$ heterocycloalkyl, aryl, or heteroaryl;
thereby producing the compound of formula (I) in a one-pot reaction.

2. The method of claim 1, wherein A is phenyl.
3. The method of claim 2, wherein n is 1.
4. The method of claim 3, wherein $R_1$ is at o-position.
5. The method of claim 4, wherein $R_1$ is $C_1$–$C_{10}$ alkyl, halo, or $OR_a$.
6. The method of claim 5, wherein $R_1$ is $CH_3$, $CF_3$, Cl, or $OCH_3$.
7. The method of claim 3, wherein $R_1$ is at m-position.
8. The method of claim 7, wherein $R_1$ is $C_1$–$C_{10}$ alkyl.
9. The method of claim 8, wherein $R_1$ is $CH_3$.

10. The method of claim 3, wherein $R_1$ is at p-position.
11. The method of claim 10, wherein $R_1$ is $OR_a$.
12. The method of claim 11, wherein $R_1$ is $OC_{12}H_{25}$.
13. A compound of formula (I):

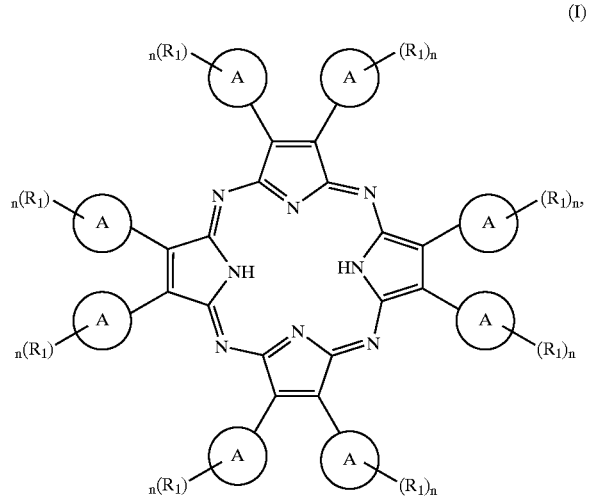

(I)

wherein
 each A is phenyl;
 each n, independently, is 1–5; and
 each $R_1$, independently, is $C_1$–$C_{10}$ alkyl, $C_3$–$C_{20}$ cycloalkyl, $C_3$–$C_{20}$ heterocycloalkyl, aryl, heteroaryl, halo, cyano, nitro, $OR_a$, $NR_aR_b$, $SiR_aR_bR_c$, $COOR_a$, $OC(O)R_a$, $C(O)NR_aR_b$, $N(R_a)$—$C(O)R_b$, or —$SO_3R_a$;
 at least one $R_1$ being at one of the two o-positions of each A; provided that when $R_1$ is Br or $CH_3$, n is 1; or a metal complex thereof.

14. The compound of claim 13, wherein n is 1.

15. The compound of claim 14, wherein $R_1$ is $C_1$–$C_{10}$ alkyl, halo, or $OR_a$.

16. The compound of claim 15, wherein $R_1$ is $CH_3$, $CF_3$, Cl, or $OCH_3$.

17. The compound of claim 16, wherein the compound is a metal complex containing $Zn^{2+}$, $Ni^{2+}$, $Pd^{2+}$, or $Al^{3+}$.

18. The compound of claim 16, wherein the compound is

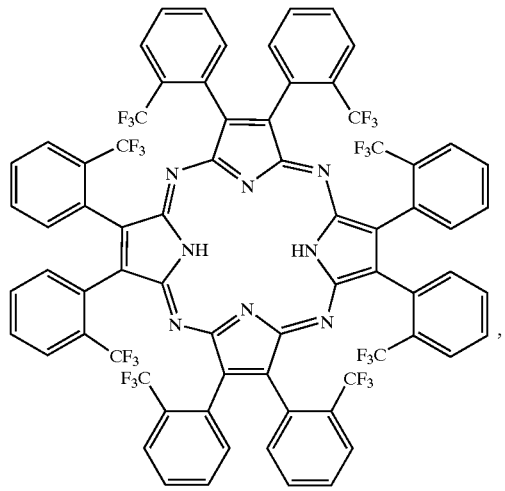

,

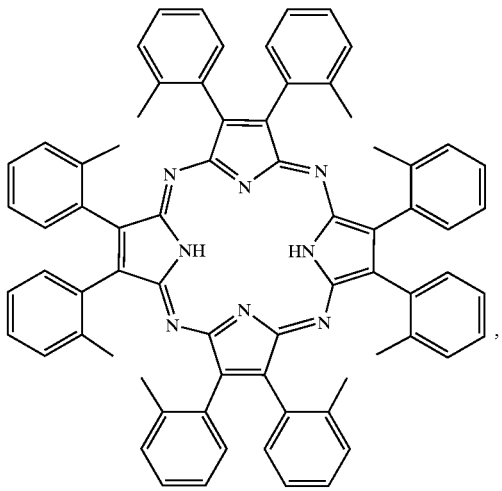

,

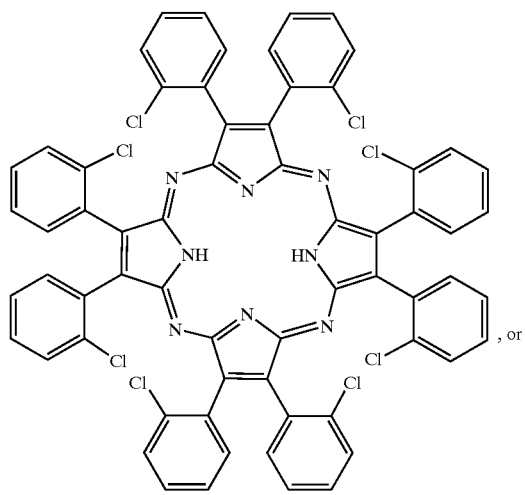

, or

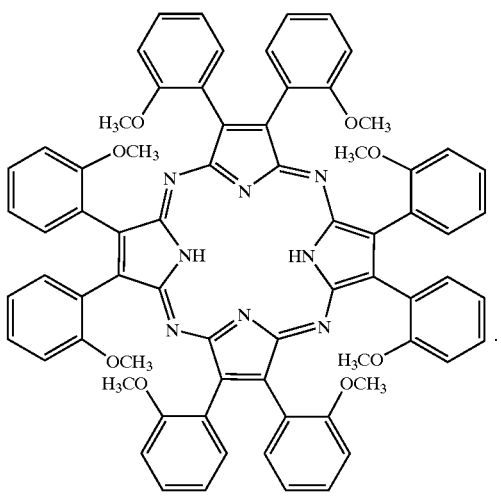

.

19. The compound of claim 17, wherein the compound is

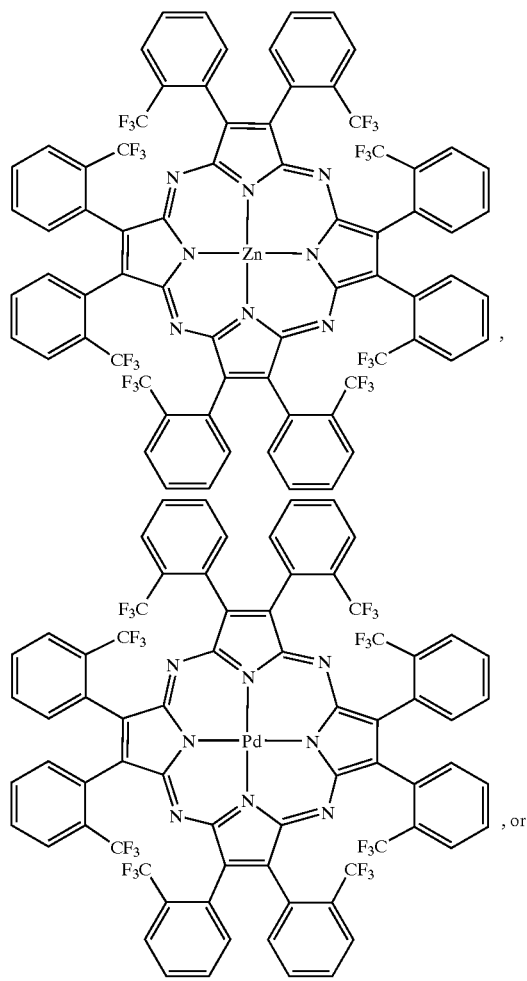, or

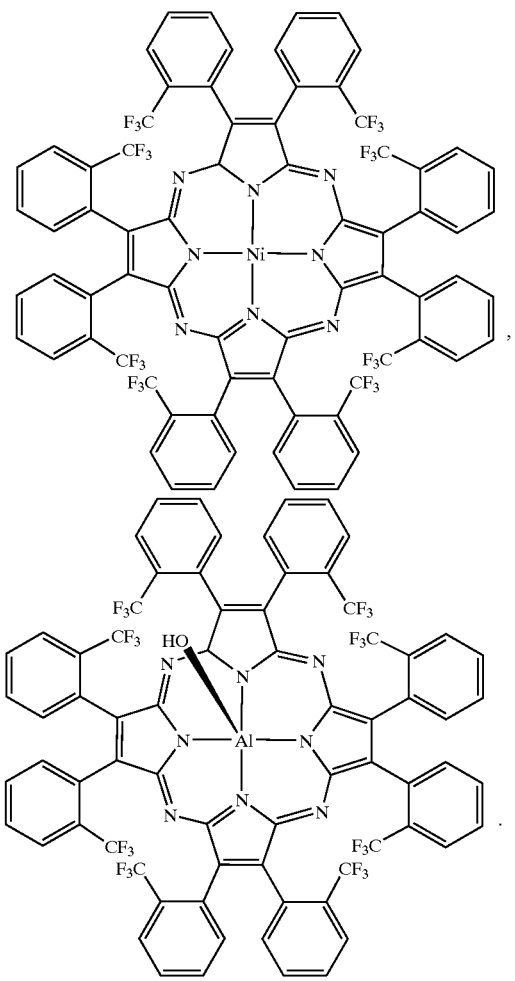.

20. The compound of claim 13, wherein the compound is a metal complex containing $Zn^{2+}$, $Ni^{2+}$, $Pd^{2+}$, $Al^{3+}$, or $Mg^{2+}$.

21. A compound of formula (I):

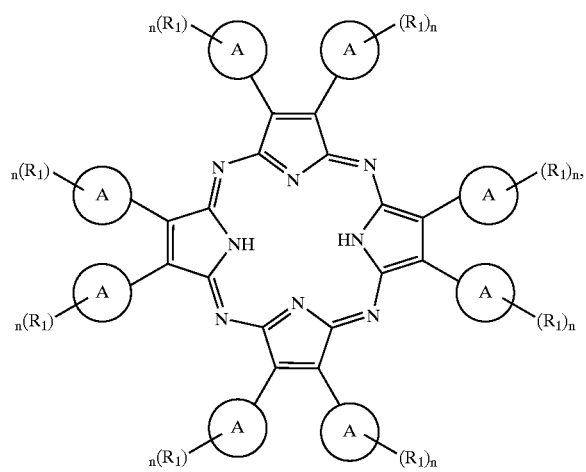

(I)

wherein each A, independently, is heteroaryl or fused aryl;

each n, independently, is 1–3; and each $R_1$, independently, is $C_5$–$C_{10}$ alkyl, $C_3$–$C_{20}$ cycloalkyl.

22. The compound of claim 21, wherein n is 1.

23. The compound of claim 22, wherein $R_1$ is $C_5$–$C_{10}$ alkyl, halo, or $OR_a$.

24. The compound of claim 23, wherein the compound is a metal complex containing $Zn^{2+}$, $Ni^{2+}$, $Pd^{2+}$, $Al^{3+}$, or $Mg^{2+}$.

25. The compound of claim 21, wherein the compound is a metal complex containing $Zn^{2+}$, $Ni^{2+}$, $Pd^{2+}$, $Al^{3+}$, or $Mg^{2+}$.

* * * * *